United States Patent
Wong et al.

(10) Patent No.: US 10,817,102 B2
(45) Date of Patent: Oct. 27, 2020

(54) INPUT DEVICE FOR ELECTRONIC DEVICES

(71) Applicant: INTEL CORPORATION, Santa Clara, CA (US)

(72) Inventors: Hong W. Wong, Portland, OR (US); Wah Yiu Kwong, Hillsboro, OR (US); Xiaoguo Liang, Shanghai (CN); Jiancheng Tao, Shanghai (CN); Yanbing Sun, Shanghai (CN)

(73) Assignee: INTEL CORPORATION, Santa Clara, CA (US)

( * ) Notice: Subject to any disclaimer, the term of this patent is extended or adjusted under 35 U.S.C. 154(b) by 0 days.

(21) Appl. No.: 16/086,475

(22) PCT Filed: Jun. 21, 2016

(86) PCT No.: PCT/CN2016/086502
§ 371 (c)(1),
(2) Date: Sep. 19, 2018

(87) PCT Pub. No.: WO2017/219221
PCT Pub. Date: Dec. 28, 2017

(65) Prior Publication Data
US 2019/0102029 A1    Apr. 4, 2019

(51) Int. Cl.
*G06F 3/041* (2006.01)
*A61F 4/00* (2006.01)
(Continued)

(52) U.S. Cl.
CPC ............ *G06F 3/04144* (2019.05); *A61F 4/00* (2013.01); *G06F 1/169* (2013.01); *G06F 1/1643* (2013.01);
(Continued)

(58) Field of Classification Search
CPC ....... G06F 3/0414–04146; G06F 3/041; G06F 3/0412; G06F 1/169; G06F 3/1643; H03K 19/1733; H04R 1/04
See application file for complete search history.

(56) References Cited

U.S. PATENT DOCUMENTS 5,603,065 A * 2/1997 Baneth ..................... A61F 4/00
340/4.14
6,574,571 B1 * 6/2003 Bonnat .................... G10H 3/16
345/163
(Continued)

FOREIGN PATENT DOCUMENTS

CN    101714047 A    5/2010
CN    102707805 B    9/2015
(Continued)

OTHER PUBLICATIONS

International Search Report and Written Opinion for PCT Application No. PCT/CN2016/086502, 12 pages, dated Mar. 13, 2017.

Primary Examiner — David Tung
(74) Attorney, Agent, or Firm — Jaffery Watson Mendonsa & Hamilton LLP

(57) ABSTRACT

In one example a input device for an electronic device comprises a first panel comprising an array of pressure sensors, a second panel comprising an array of apertures in fluid communication with the pressure sensors, and a controller comprising logic, at least partly including hardware logic, to receive a plurality of output signals from the plurality of pressure sensors, determine, from the plurality of output signals, a location of an input on the second panel, and generate a data point on a bitmap corresponding to the location of the input on the second panel. Other examples may be described.

9 Claims, 11 Drawing Sheets

(51) Int. Cl.
*G06F 3/01* (2006.01)
*G06F 1/16* (2006.01)
*H03K 19/173* (2006.01)
*H04R 1/04* (2006.01)

(52) U.S. Cl.
CPC ............ *G06F 3/011* (2013.01); *G06F 3/0414* (2013.01); *H03K 19/1733* (2013.01); *H04R 1/04* (2013.01)

(56) References Cited

U.S. PATENT DOCUMENTS

| | | | |
|---|---|---|---|
| 8,213,634 B1 * | 7/2012 | Daniel | H04R 3/005 381/122 |
| 8,531,429 B2 | 9/2013 | Chang | |
| 2005/0268247 A1 * | 12/2005 | Baneth | G06F 3/04886 715/781 |
| 2006/0142957 A1 * | 6/2006 | Bonnat | G06F 3/002 702/50 |
| 2006/0177085 A1 * | 8/2006 | Izuchi | H04R 1/086 381/369 |
| 2012/0111660 A1 * | 5/2012 | Huettner | G10K 11/172 181/196 |
| 2014/0152603 A1 | 6/2014 | Algreatly | |
| 2014/0176489 A1 * | 6/2014 | Park | G06F 3/044 345/174 |

FOREIGN PATENT DOCUMENTS

| | | |
|---|---|---|
| CN | 109313481 A | 2/2019 |
| DE | 11 2016 006 987 A | 4/2019 |
| JP | 2009230534 A | 10/2009 |

* cited by examiner

FIG. 1    ELECTRONIC DEVICE 100

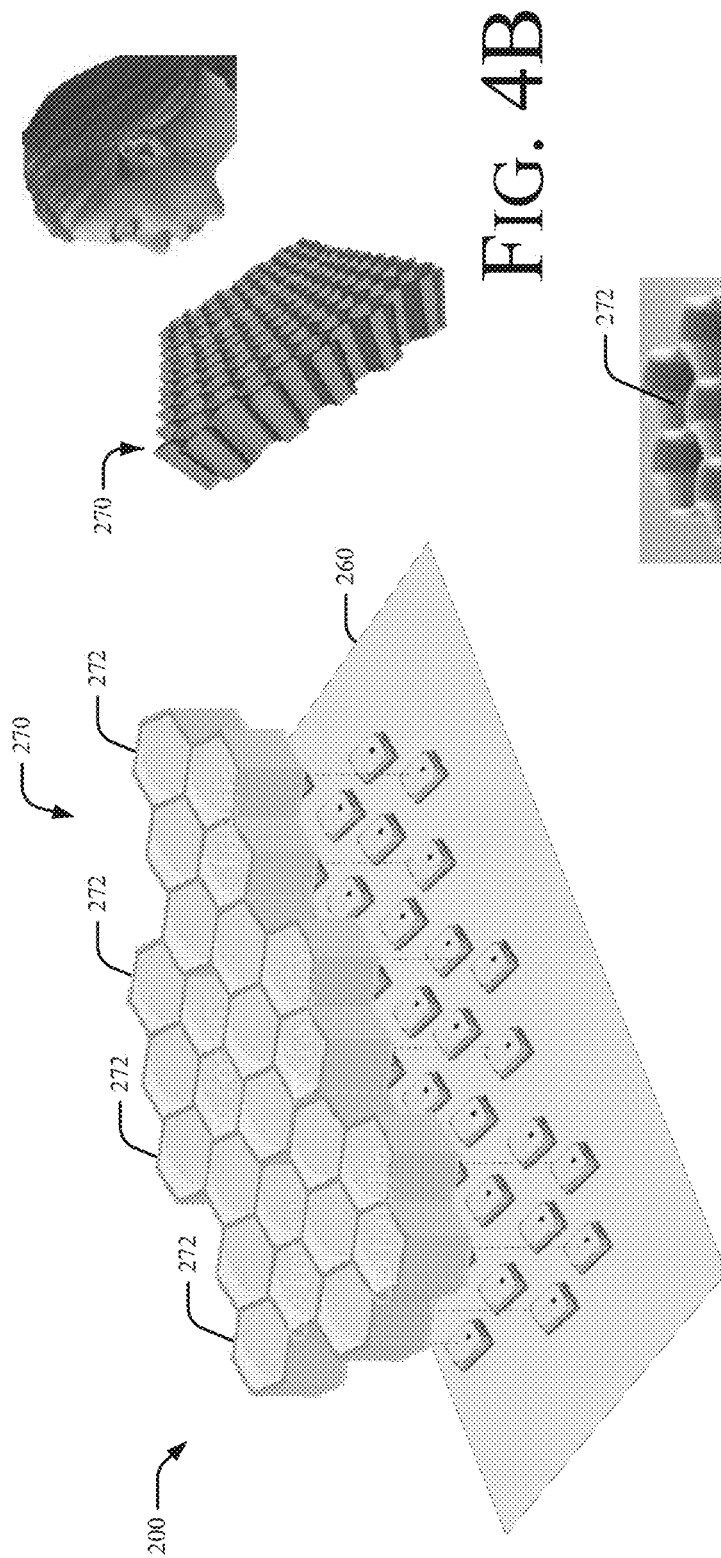
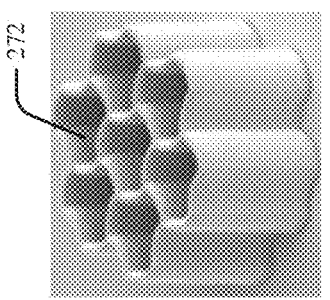
FIG. 4A
FIG. 4B
FIG. 4C

INPUT DEVICE FOR ELECTRONIC DEVICES

BACKGROUND

This application claims the benefit of priority under 35 U.S.C. § 371 to International Application No. PCT/CN2016/086502 filed Jun. 21, 2016, entitled INPUT DEVICE FOR ELECTRONIC DEVICES, the disclosure of which is incorporated herein by reference in its entirety.

The subject matter described herein relates generally to the field of electronic devices and more particularly to an input device for electronic devices.

Electronic devices, e.g., computer systems, tablet devices, smart phones and the like commonly include input devices such as keyboards and/or touch screen devices which require physical interaction with the input device. Such input devices raise challenges for persons who suffer from severe physical disabilities. Accordingly, additional input devices for electronic devices may find utility.

BRIEF DESCRIPTION OF THE DRAWINGS

The detailed description is described with reference to the accompanying figures.

FIGS. 4A, 4B, and 4C are schematic views of components of a input device adapted for use with an electronic device in accordance with some examples.

DETAILED DESCRIPTION

Described herein are exemplary systems and methods to implement a input device in electronic devices. In the following description, numerous specific details are set forth to provide a thorough understanding of various examples. However, it will be understood by those skilled in the art that the various examples may be practiced without the specific details. In other instances, well-known methods, procedures, components, and circuits have not been illustrated or described in detail so as not to obscure the particular examples.

As described above, it may be useful to provide input devices for electronic device(s) which do not require physical contact to provide inputs. In some examples the subject matter described herein addresses these and other issues by providing an input device for an electronic device which comprises a first panel comprising an array of pressure sensors, a second panel comprising an array of apertures with duct works to transfer the pressure to the pressure sensors, and a controller comprising logic, at least partly including hardware logic, to receive a plurality of output signals from the plurality of pressure sensors, determine, from the plurality of output signals, a location of an input on the second panel, and generate a data point on a bitmap corresponding to the location of the input on the second panel.

In another example, an input device for an electronic device comprises a first panel comprising an array of microphones, a second panel comprising an array of boots to channel the sound created when air passing thru the boots, to the array of microphones, and a controller comprising logic, at least partly including hardware logic, to receive a plurality of output signals from the plurality of microphones, determine, from the plurality of output signals, a location of an input on the second panel and generate a data point on a bitmap corresponding to the location of the input on the second panel.

In some examples a user may provide an input to the input device by blowing on the second panel of the input device. In examples in which the first panel includes an array of pressure sensors, the pressure sensors detect an increase in pressure on areas of the second panel to which airflow is directed. In examples in which the first panel includes an array of microphones the microphones detect resonance generated by airflow through boots in the first panel.

In some examples the controller on the input device may collect data for input locations over time and may process the location data to determine whether an input corresponds to a predetermined symbol, e.g., an alphanumeric character or the like. Optionally, the symbol may be presented on an output device, e.g., a display.

Additional features and operating characteristics of the electronic device and associated system are described below with reference to FIGS. 1-10.

Figure 1:
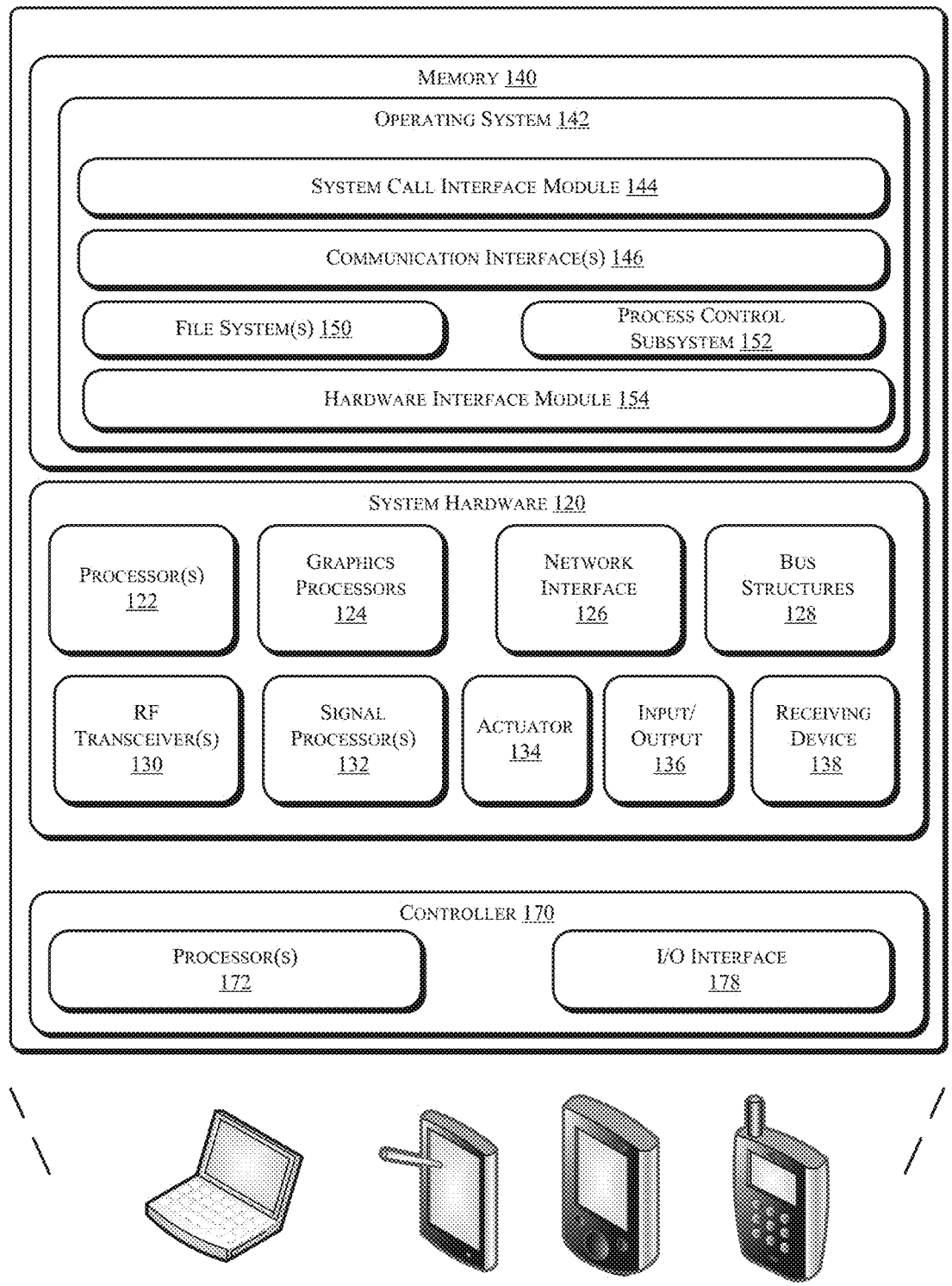
FIG. 1 is a schematic illustration of an electronic device which may be adapted to work with input devices in accordance with some examples.
Figure 2:
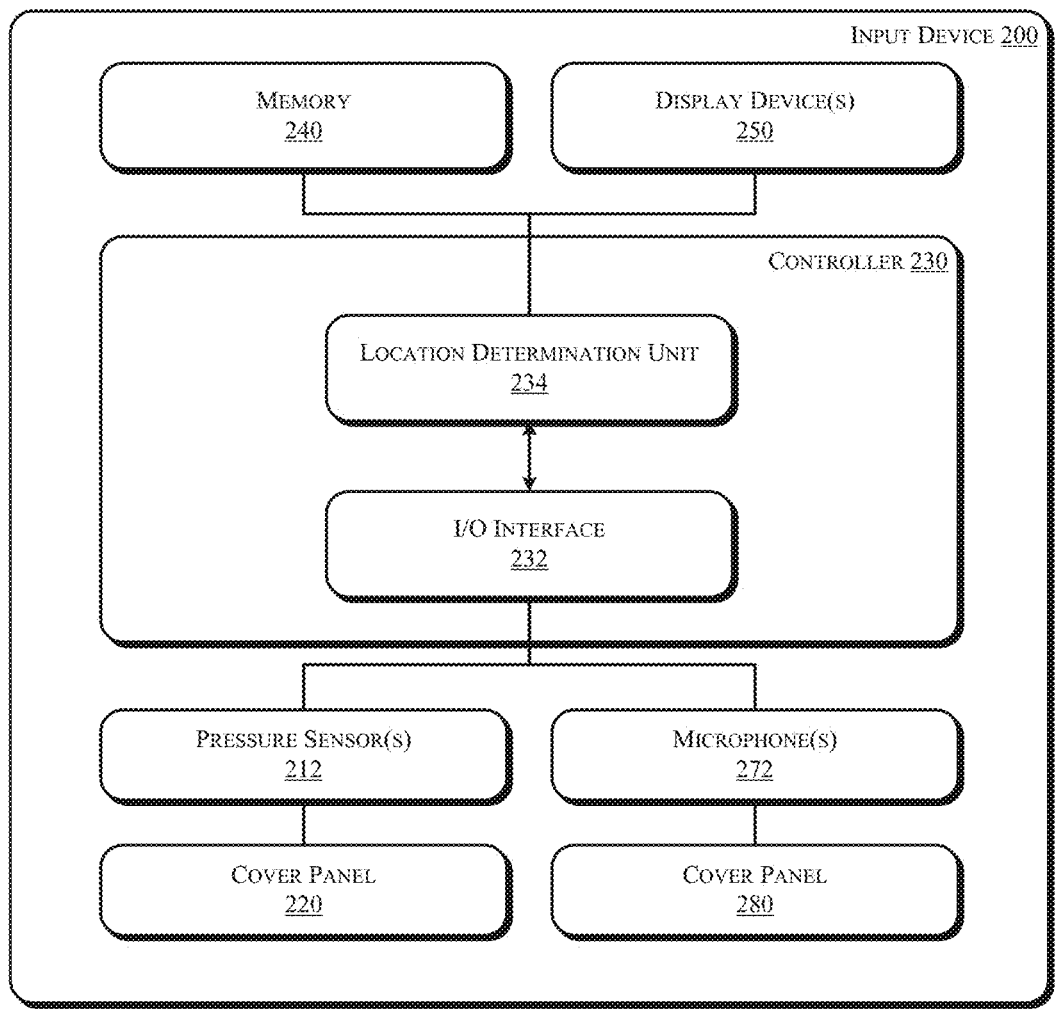
FIG. 2 is a high-level schematic illustration of an input device adapted for use with an electronic device in accordance with some examples.

FIG. 1 is a schematic illustration of an electronic device 100 which may be adapted to include one or more input devices in accordance with some examples. In various examples, electronic device 100 may include or be coupled to one or more accompanying input/output devices including a display, one or more speakers, a keyboard, one or more other I/O device(s), a mouse, a camera, or the like. Other exemplary I/O device(s) may include a touch screen, a voice-activated input device, a track ball, a geolocation device, an accelerometer/gyroscope, biometric feature input devices, and any other device that allows the electronic device 100 to receive input from a user.

The electronic device 100 includes system hardware 120 and memory 140 which may be implemented as random access memory and/or read-only memory. A file store may be communicatively coupled to electronic device 100. The file store may be internal to electronic device 100 such as, e.g., eMMC, SSD, one or more hard drives, or other types of storage devices. Alternatively, the file store may also be external to electronic device 100 such as, e.g., one or more external hard drives, network attached storage, or a separate storage network.

System hardware 120 may include one or more processors 122, graphics processors 124, network interfaces 126, and bus structures 128. In one embodiment, processor 122 may be embodied as an Intel® Atom™ processors, Intel® Atom™ based System-on-a-Chip (SOC) or Intel® Core2 Duo® or i3/i5/i7 series processor available from Intel Corporation, Santa Clara, Calif., USA. As used herein, the term "processor" means any type of computational element, such as but not limited to, a microprocessor, a microcontroller, a complex instruction set computing (CISC) microprocessor, a reduced instruction set (RISC) microprocessor, a very long instruction word (VLIW) microprocessor, or any other type of processor or processing circuit.

Graphics processor(s) 124 may function as adjunct processor that manages graphics and/or video operations. Graphics processor(s) 124 may be integrated onto the motherboard of electronic device 100 or may be coupled via an expansion slot on the motherboard or may be located on the same die or same package as the Processing Unit.

In one embodiment, network interface 126 could be a wired interface such as an Ethernet interface (see, e.g., Institute of Electrical and Electronics Engineers/IEEE 802.3-2002) or a wireless interface such as an IEEE 802.11a, b or g-compliant interface (see, e.g., IEEE Standard for IT-Telecommunications and information exchange between systems LAN/MAN-Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a general packet radio service (GPRS) interface (see, e.g., Guidelines on GPRS Handset Requirements, Global System for Mobile Communications/GSM Association, Ver. 3.0.1, December 2002).

Bus structures 128 connect various components of system hardware 128. In one embodiment, bus structures 128 may be one or more of several types of bus structure(s) including a memory bus, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI), a High Speed Synchronous Serial Interface (HSI), a Serial Low-power Inter-chip Media Bus (SLIMbus®), or the like.

Electronic device 100 may include an RF transceiver 130 to transceive RF signals, and a signal processing module 132 to process signals received by RF transceiver 130. RF transceiver may implement a local wireless connection via a protocol such as, e.g., Bluetooth or 802.11X. IEEE 802.11a, b or g-compliant interface (see, e.g., IEEE Standard for IT-Telecommunications and information exchange between systems LAN/MAN-Part II: Wireless LAN Medium Access Control (MAC) and Physical Layer (PHY) specifications Amendment 4: Further Higher Data Rate Extension in the 2.4 GHz Band, 802.11G-2003). Another example of a wireless interface would be a WCDMA, LTE, general packet radio service (GPRS) interface (see, e.g., Guidelines on GPRS Handset Requirements, Global System for Mobile Communications/GSM Association, Ver. 3.0.1, December 2002).

Electronic device 100 may further include one or more power storage devices 134, e.g., batteries, and one or more input/output interfaces 136 such as, e.g., a keypad and/or a display. In some examples electronic device 100 may not have a keypad and use the touch panel for input.

Electronic device 100 may further include at least one wireless power receiving device 138 to receive power via an electromagnetic coupling with a driven coil in a charging device. The wireless power receiving device 138 may comprise one or more coil(s) to receive power through an inductive coupling with a driven coil or coupling charge plate(s) to receive power through a capacitive coupling with a driven capacitor in the charging device.

Memory 140 may include an operating system 142 for managing operations of electronic device 100. In one embodiment, operating system 142 includes a hardware interface module 154 that provides an interface to system hardware 120. In addition, operating system 140 may include a file system 150 that manages files used in the operation of electronic device 100 and a process control subsystem 152 that manages processes executing on electronic device 100.

Operating system 142 may include (or manage) one or more communication interfaces 146 that may operate in conjunction with system hardware 120 to send and/or receive data packets and/or data streams from a remote source. Operating system 142 may further include a system call interface module 144 that provides an interface between the operating system 142 and one or more application modules resident in memory 140. Operating system 142 may be embodied as a UNIX operating system or any derivative thereof (e.g., Linux, Android, etc.) or as a Windows® brand operating system, or other operating systems.

In some examples an electronic device may include a controller 170, which may comprise one or more controllers that are separate from the primary execution environment. The separation may be physical in the sense that the controller may be implemented in controllers which are physically separate from the main processors. Alternatively, the trusted execution environment may logical in the sense that the controller may be hosted on same chip or chipset that hosts the main processors.

By way of example, in some examples the controller 170 may be implemented as an independent integrated circuit located on the motherboard of the electronic device 100, e.g., as a dedicated processor block on the same SOC die. In other examples the trusted execution engine may be implemented on a portion of the processor(s) 122 that is segregated from the rest of the processor(s) using hardware enforced mechanisms In the embodiment depicted in FIG. 1 the controller 170 comprises a processor 172, and an I/O interface 178. The I/O module 178 may comprise a serial I/O module or a parallel I/O module. Because the controller 170 is separate from the main processor(s) 122 and operating system 142, the controller 170 may be made secure, i.e., inaccessible to hackers who typically mount software attacks from the host processor 122. In some examples portions of the charge manager 176 may reside in the memory 140 of electronic device 100 and may be executable on one or more of the processors 122.

Aspects of an input device will be explained with reference to FIGS. 2, 3A-3B, and 4A-4C. In some examples an input device 200 includes a first panel 210 comprising a two-dimensional array of pressure sensors 212 and a second panel 220 comprising a two-dimensional array of apertures 222 and a plurality of ducts (e.g., tubing) 224 extending between the array of pressure sensors 212 and the array of apertures 222 (FIG. 3A).

Figure 3A:
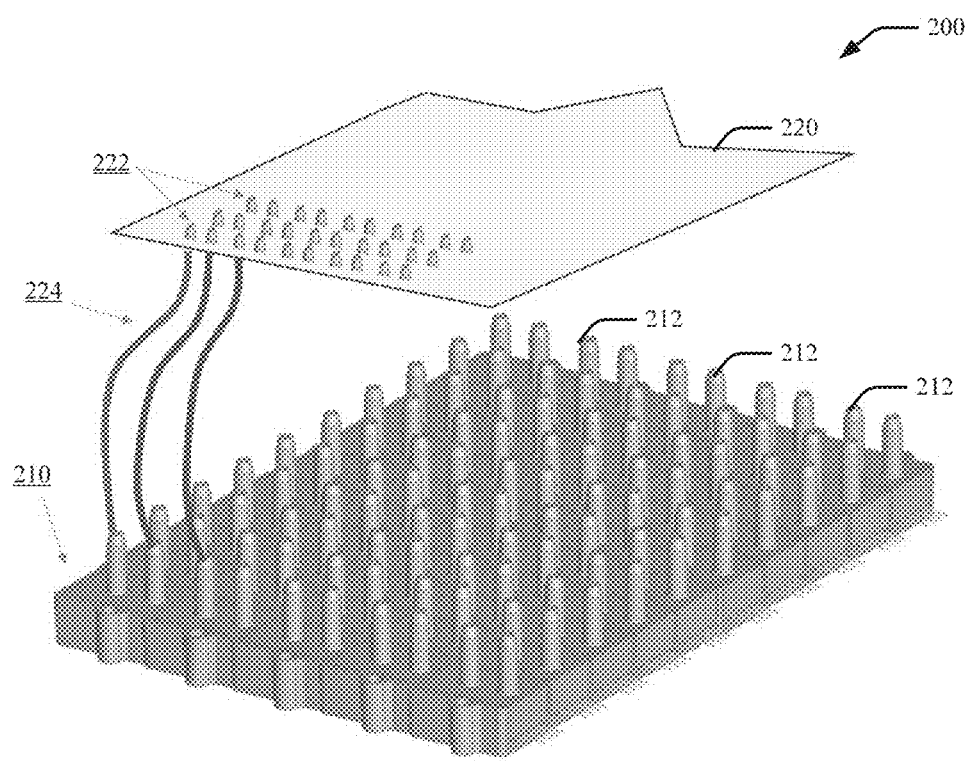
FIGS. 3A and 3B are schematic views of a input device adapted for use with an electronic device in accordance with some examples.
Figure 3B:
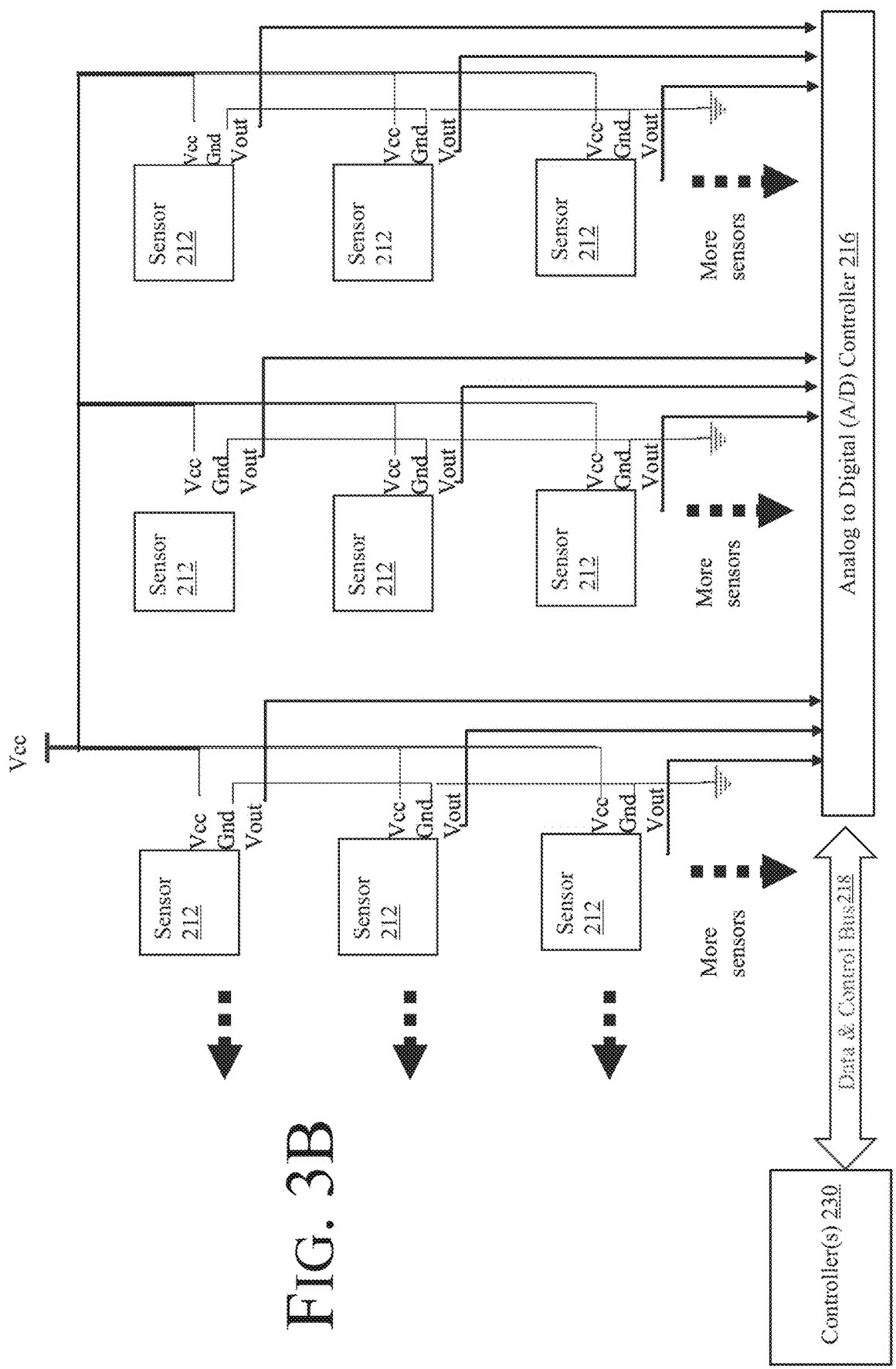

Referring to FIGS. 3A-3B, in some examples the first panel 210 may be formed from a plurality of plurality of pressure sensors 212 arranged into a two dimensional array (e.g., an MxN array). Each sensor 212 may be coupled to an operating voltage source (Vcc) and to a ground (Gnd). Further, each sensor 212 may generate an output signal, a voltage (Vout) that is function of pressure applied to the sensor 212. The output voltages (Vout) of the respective sensors 212 may be input to an analog to digital (A/D) controller 216, which converts the respective analog voltages (Vout) to a digital signal which may be transmitted via a data bus 218 to a controller 230.

In some examples the second panel 220 may be formed from a suitably rigid material, e.g., a polymer or a glass material. In some examples the ducts 224 provide an airflow passage between the respective apertures 222 and at least one pressure sensor 212 on the first panel 210. The ducts 224 may be implemented as tubes or channels formed from a suitable material, e.g., a polymer or rubber. Further, the ducts may be formed as an integral part of second panel 220 or as a separate entity.

In alternate examples the input device 200 may be formed without a second panel 220. In such examples the various sensors 212 on the first panel 210 may be exposed directly to the ambient environment.

Referring briefly to FIGS. 4A-4C, in another example the input device 200 comprises a first panel 260 comprising a two dimensional array of microphones 262 and a second panel 270 comprising a two dimensional array of boots 272 in fluid communication with the microphones 262. The second panel 270 may be configured to fit over the first panel 260 such that each of the boots 272 fits over a respective microphone 262.

In some examples the boots 272 may be implemented as airflow channels and may be of uniform configuration, e.g., a hexagonal configuration as depicted in FIG. 4A or a modified hexagon as depicted in FIG. 4C. In other examples the boots 272 may be implemented as airflow channels formed in a plurality of different configurations to generate a plurality of different frequency outputs in response to airflow incident upon the respective boots 272. For example, each of the boots 272 may be formed to a different size and/or shape, or from a different material, to generate a unique pitch r e in response to airflow directed into the boots 272. Similarly, the microphones 262 may be tuned to receive a specific pitch and/or tone of sound generated by airflow through the boots 272 or by another device in the ambient environment.

Referring back to FIG. 2, in some examples the input device 200 comprises a controller 230 which, in turn, comprises an input/output interface 232 and a location determination unit 234. In some examples the input device 200 may comprise, or be communicatively coupled to, a memory 240 and one or more display devices 250.

Having described structural components of a input device, various operations of a input device 200 will be described with reference to FIG. 5. In some examples one or more components of input device cooperate with components of the electronic device 100 to enable input device 200 to generate inputs for electronic device 100.

Figure 5:
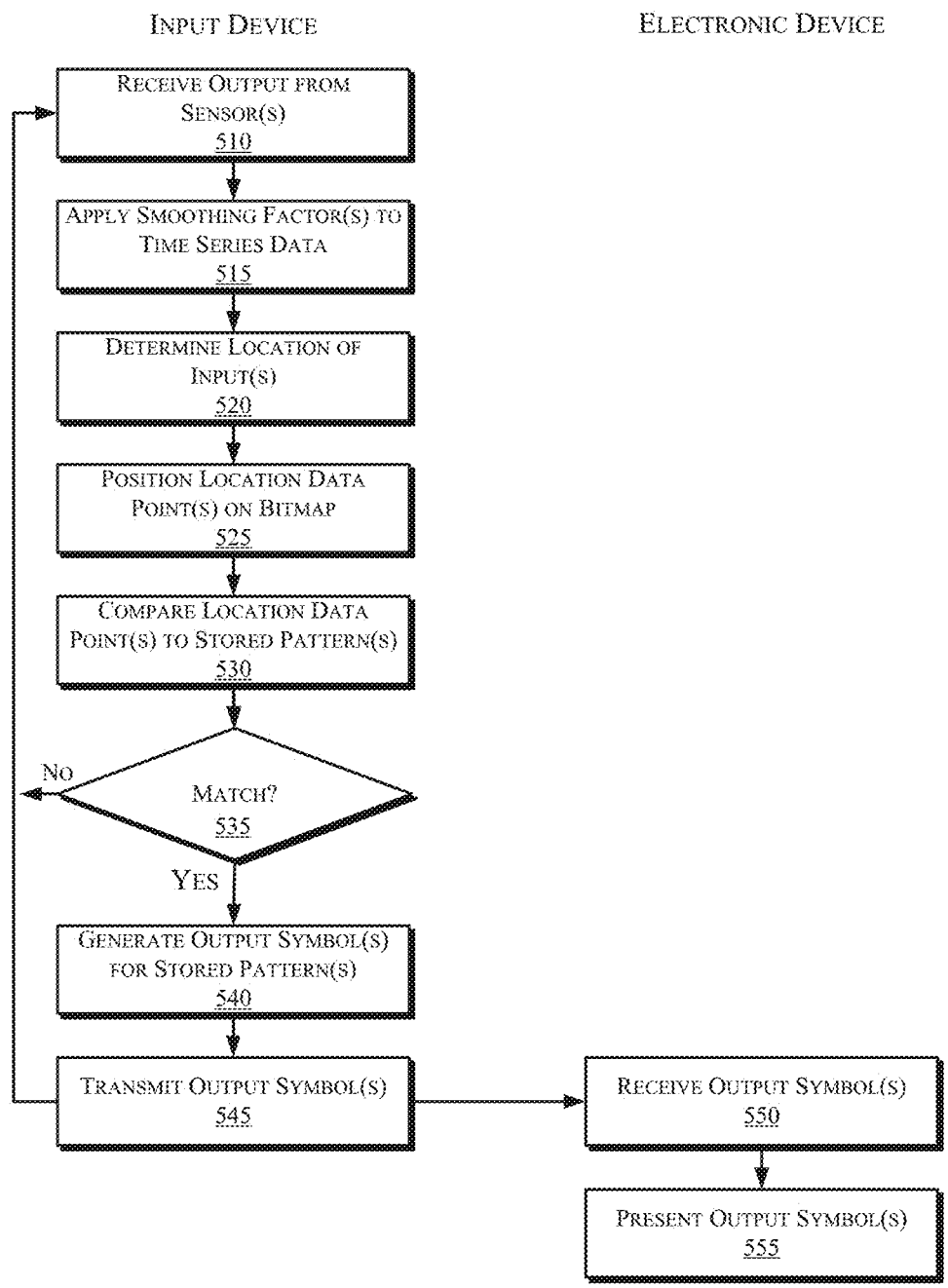
FIG. 5 is a flowchart illustrating operations in a method to operate a input device in accordance with some examples.

Referring to FIG. 5, at operation 510 the controller 230 receives an output from one or more of the sensor(s) 212, 262 in the input device 200. By way of example, in the pressure sensor embodiment depicted in FIGS. 3A-3B the pressure sensors 212 may generate an output in response to pressure generated when air is forced through the apertures 222 and the ducts 224, e.g., when a user blows on the surface of the second panel 220. By contrast, in the microphone embodiment depicted in FIGS. 4A-4C the microphones 262 may generate an output in response to turbulence generated in the boots 272 when air is forced into the boots, e.g., when a user blows on the surface of the second panel 270 as illustrated in FIG. 4C.

In some examples the controller 230 samples the outputs from the respective sensors on a period basis over a period of time and stores the outputs in memory 240 as a time series data set of inputs to the sensors. The time series data set may include the output of the sensor, an identifier and associated with the sensor, and a location of the sensor on the input device 200. Thus, when the sensors are arranged in a two dimensional array the time series data set captures pressure variations in time across points on the surface of the input device 200.

At operation 515 the controller 230 may apply one or more smoothing factors to the time series data set. By way of example, a smoothing factor may filter outputs from the pressure sensor(s) 212 which are of substantially greater magnitude than the average output of the data set. Abnormally large outputs from pressure sensors 212 may be associated with unintentional physical impacts by an object on the input device 200 and may be discarded from the data set. Similarly, a smoothing factor may filter outputs from microphones 262 which are substantially of substantially greater magnitude than the average output of the data set. Abnormally large outputs from microphones 262 may be associated with unintentional noise inputs to the input device such as sneezing or coughing and may be discarded from the data set.

At operation 520 the controller 230 in the input device 200 determines a location of the input(s) to the input device. As described above, when the sensors 212, 262 are arranged in a two dimensional array the location information associated with sensor output information may be used to determine the location of pressure applied to the surface of the input device 200.

At operation 525 the controller 230 in the input device 200 positions the location data points determined in operation 525 on a bitmap. In some examples the bitmap may represent the surface of the input device 200.

At operation 530 the controller 230 compares the location data generated in operation 525 to one or more stored patterns in memory 240. In some examples the memory 240 may comprise bitmaps of predetermined patterns, e.g., alphanumeric characters, symbols, or the like, stored in memory 240. If, at operation 535, the controller 200 determines there is no match between the input location data generated in operation 525 and one or more stored patterns then control passes back to operation 510 and the controller 230 in the input device continues to monitor outputs from the sensors on input device 200.

By contrast, if at operation 535 the controller 230 generates one or more output symbols corresponding to the stored pattern(s) for which a match was determined in operation 535. For example, the controller 230 may generate an American Standard Code for Information Interchange (ASCII) code for the symbol(s) corresponding to the stored pattern(s) for which a match was determined in operation 535. At operation 545 the controller 230 transmits the output symbol(s) to an electronic device 100.

At operation 550 the electronic device 100 receives the output symbol(s) from the input device 200, and at operation 555 the electronic device 100 presents the output symbol(s) on an input/output device 136, e.g., on a display.

Thus, the operations depicted in FIG. 5 enable a user of the input device 200 to generate inputs for an electronic device 100 without having to make physical contact with the input device, e.g., by blowing on the surface of the input device 200.

Figure 6:
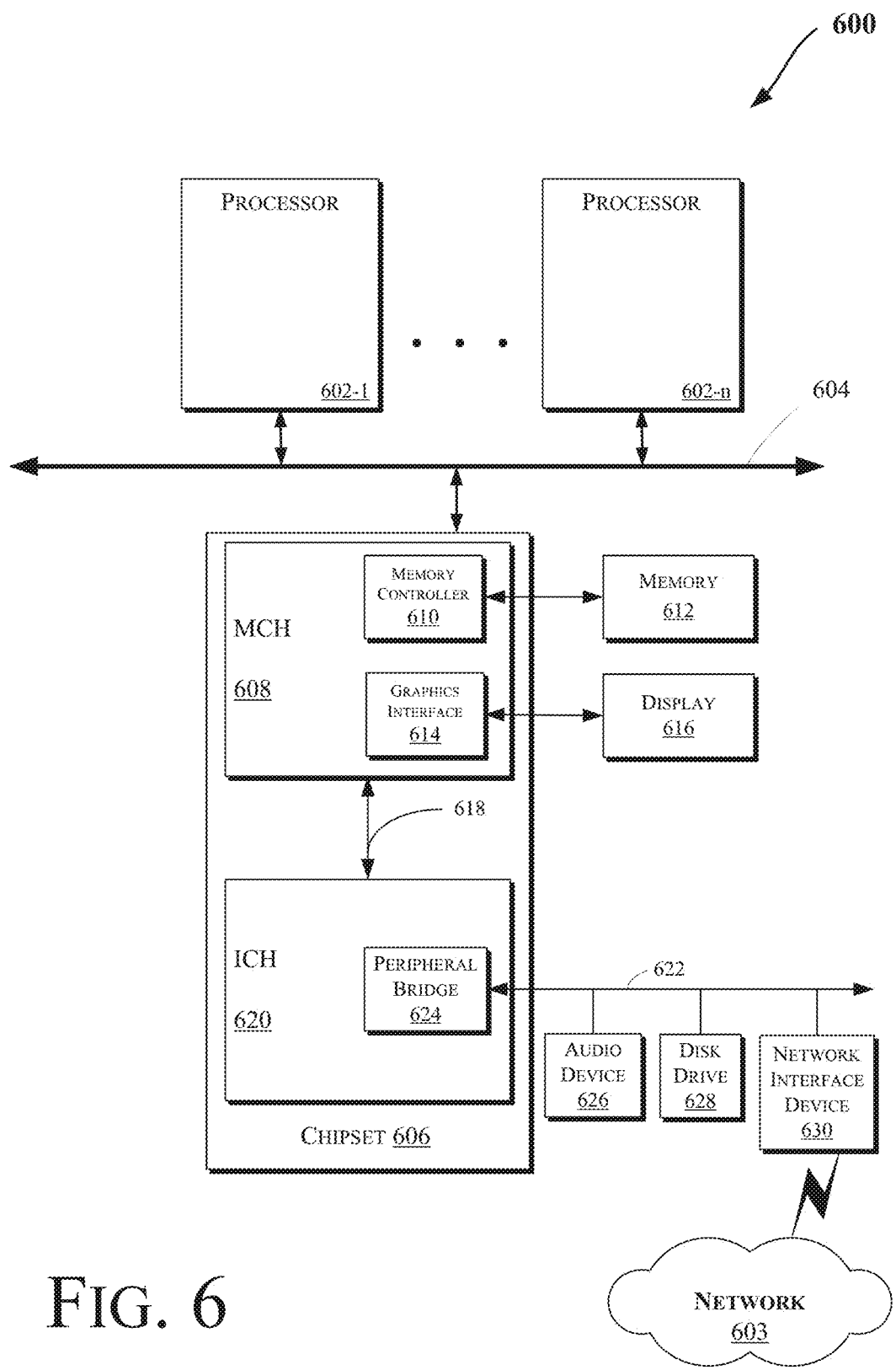
FIGS. 6-10 are schematic illustrations of electronic devices which may be adapted to mate with a input device in accordance with some examples.

As described above, in some examples the electronic device may be embodied as an information processing system. FIG. 6 illustrates a block diagram of an information processing system 600 in accordance with an example. The information processing system 600 may include one or more central processing unit(s) 602 or processors that communicate via an interconnection network (or bus) 604. The processors 602 may include a general purpose processor, a network processor (that processes data communicated over a computer network 603), or other types of a processor (including a reduced instruction set computer (RISC) processor or a complex instruction set computer (CISC)). Moreover, the processors 602 may have a single or multiple core design. The processors 602 with a multiple core design may integrate different types of processor cores on the same integrated circuit (IC) die. Also, the processors 602 with a multiple core design may be implemented as symmetrical or asymmetrical multiprocessors.

A chipset 606 may also communicate with the interconnection network 604. The chipset 606 may include a memory control hub (MCH) 608. The MCH 608 may include a memory controller 610 that communicates with a memory 612. The memory 412 may store data, including sequences of instructions, that may be executed by the processor 602, or any other device included in the computing system 600. In one example, the memory 612 may include one or more volatile storage (or memory) devices such as random access memory (RAM), dynamic RAM (DRAM), synchronous DRAM (SDRAM), static RAM (SRAM), or other types of storage devices. Nonvolatile memory may also be utilized such as a hard disk. Additional devices may communicate via the interconnection network 604, such as multiple processor(s) and/or multiple system memories.

The MCH 608 may also include a graphics interface 614 that communicates with a display device 616. In one example, the graphics interface 614 may communicate with the display device 616 via an accelerated graphics port (AGP). In an example, the display 616 (such as a flat panel display) may communicate with the graphics interface 614 through, for example, a signal converter that translates a digital representation of an image stored in a storage device such as video memory or system memory into display signals that are interpreted and displayed by the display 616. The display signals produced by the display device may pass through various control devices before being interpreted by and subsequently displayed on the display 616.

A hub interface 618 may allow the MCH 608 and an input/output control hub (ICH) 620 to communicate. The ICH 620 may provide an interface to I/O device(s) that communicate with the computing system 600. The ICH 620 may communicate with a bus 622 through a peripheral bridge (or controller) 624, such as a peripheral component interconnect (PCI) bridge, a universal serial bus (USB) controller, or other types of peripheral bridges or controllers. The bridge 624 may provide a data path between the processor 602 and peripheral devices. Other types of topologies may be utilized. Also, multiple buses may communicate with the ICH 620, e.g., through multiple bridges or controllers. Moreover, other peripherals in communication with the ICH 620 may include, in various examples, integrated drive electronics (IDE) or small computer system interface (SCSI) hard drive(s), USB port(s), a keyboard, a mouse, parallel port(s), serial port(s), floppy disk drive(s), digital output support (e.g., digital video interface (DVI)), or other devices.

The bus 622 may communicate with an audio device 626, one or more disk drive(s) 628, and a network interface device 630 (which is in communication with the computer network 603). Other devices may communicate via the bus 622. Also, various components (such as the network interface device 630) may communicate with the MCH 608 in some examples. In addition, the processor 602 and one or more other components discussed herein may be combined to form a single chip (e.g., to provide a System on Chip (SOC)). Furthermore, the graphics accelerator 616 may be included within the MCH 608 in other examples.

Furthermore, the information processing system 600 may include volatile and/or nonvolatile memory (or storage). For example, nonvolatile memory may include one or more of the following: read-only memory (ROM), programmable ROM (PROM), erasable PROM (EPROM), electrically EPROM (EEPROM), a disk drive (e.g., 628), a floppy disk, a compact disk ROM (CD-ROM), a digital versatile disk (DVD), flash memory, a magneto-optical disk, or other types of nonvolatile machine-readable media that are capable of storing electronic data (e.g., including instructions).

Figure 7:
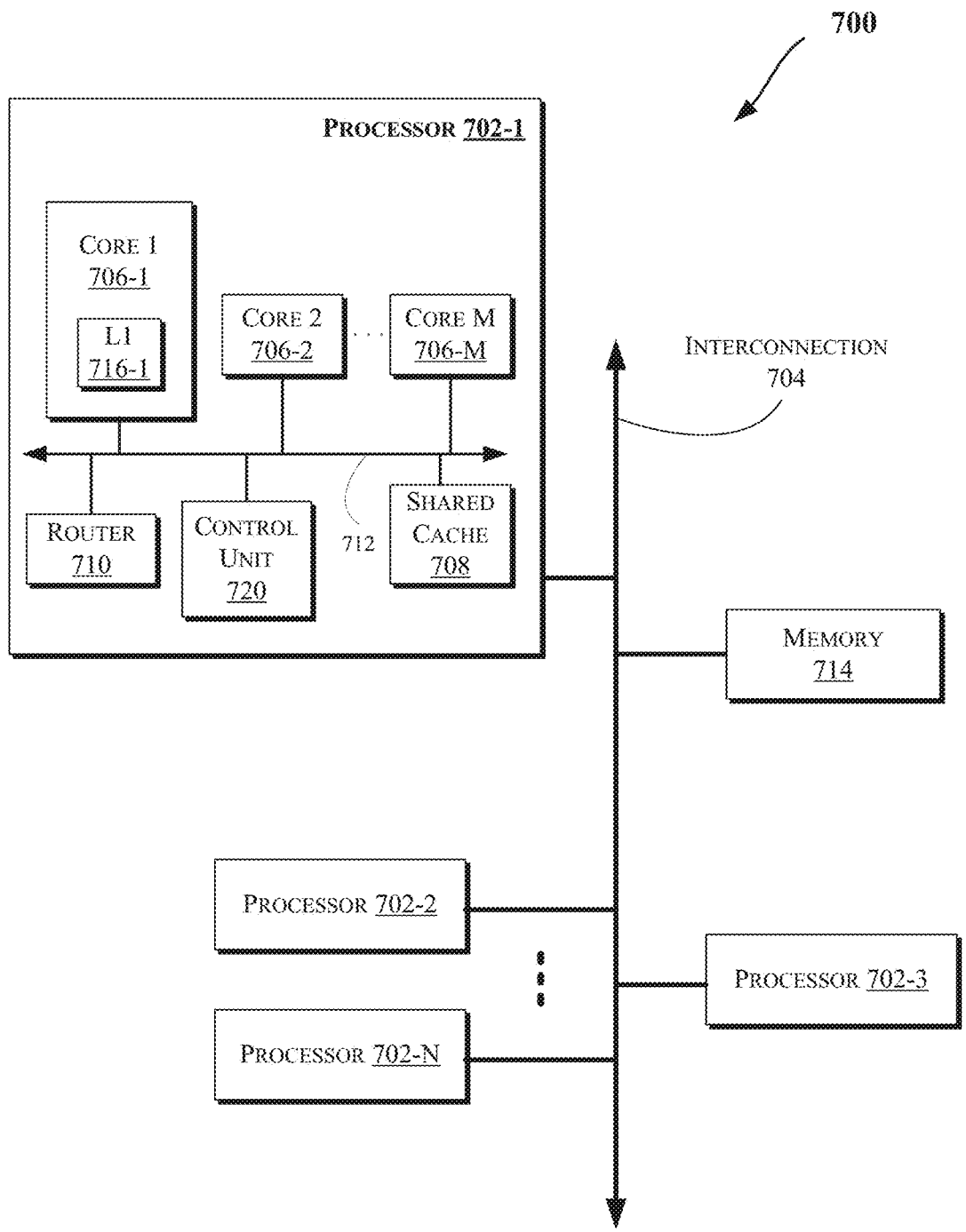

FIG. 7 illustrates a block diagram of an information processing system 700, according to an example. The information processing system 700 may include one or more processors 702-1 through 702-N (generally referred to herein as "processors 702" or "processor 702"). The processors 702 may communicate via an interconnection network or bus 704. Each processor may include various components some of which are only discussed with reference to processor 702-1 for clarity. Accordingly, each of the remaining processors 702-2 through 702-N may include the same or similar components discussed with reference to the processor 702-1.

In an example, the processor 702-1 may include one or more processor cores 706-1 through 706-M (referred to herein as "cores 706" or more generally as "core 706"), a shared cache 708, a router 710, and/or a processor control logic or unit 720. The processor cores 706 may be implemented on a single integrated circuit (IC) chip. Moreover, the chip may include one or more shared and/or private caches (such as cache 708), buses or interconnections (such as a bus or interconnection network 712), memory controllers, or other components.

In one example, the router 710 may be used to communicate between various components of the processor 702-1 and/or system 700. Moreover, the processor 702-1 may include more than one router 710. Furthermore, the multitude of routers 710 may be in communication to enable data routing between various components inside or outside of the processor 702-1.

The shared cache 708 may store data (e.g., including instructions) that are utilized by one or more components of the processor 702-1, such as the cores 706. For example, the shared cache 708 may locally cache data stored in a memory 714 for faster access by components of the processor 702. In an example, the cache 708 may include a mid-level cache (such as a level 2 (L2), a level 3 (L3), a level 4 (L4), or other levels of cache), a last level cache (LLC), and/or combinations thereof. Moreover, various components of the processor 702-1 may communicate with the shared cache 708 directly, through a bus (e.g., the bus 712), and/or a memory controller or hub. As shown in FIG. 7, in some examples, one or more of the cores 706 may include a level 1 (L1) cache 716-1 (generally referred to herein as "L1 cache 716").

Figure 8:
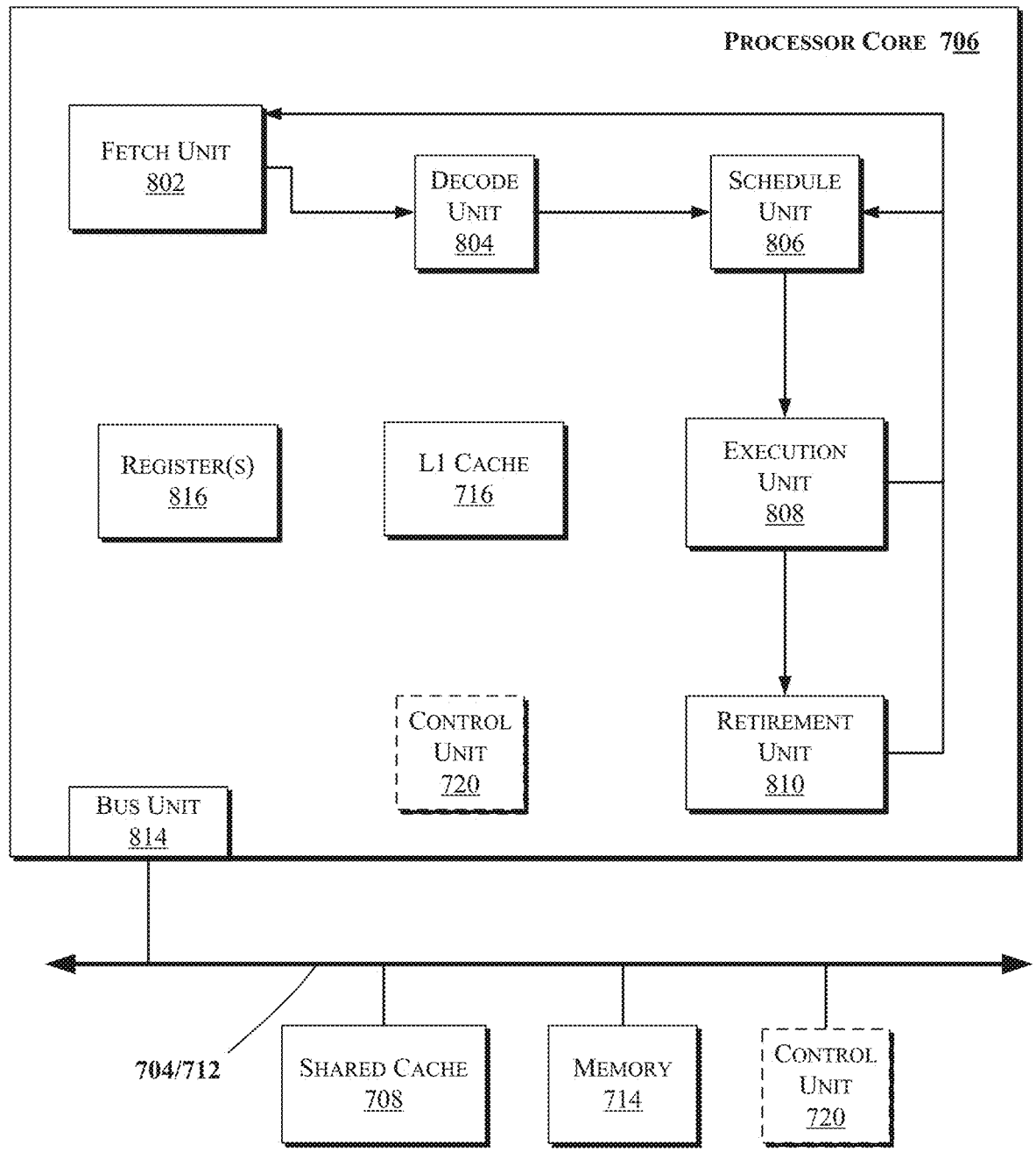

FIG. 8 illustrates a block diagram of portions of a processor core 706 and other components of an information processing system, according to an example. In one example, the arrows shown in FIG. 8 illustrate the flow direction of instructions through the core 706. One or more processor cores (such as the processor core 706) may be implemented on a single integrated circuit chip (or die) such as discussed with reference to FIG. 7. Moreover, the chip may include one or more shared and/or private caches (e.g., cache 708 of FIG. 7), interconnections (e.g., interconnections 704 of FIG. 7), control units, memory controllers, or other components.

As illustrated in FIG. 8, the processor core 706 may include a fetch unit 802 to fetch instructions (including instructions with conditional branches) for execution by the core 706. The instructions may be fetched from any storage devices such as the memory 714. The core 706 may also include a decode unit 804 to decode the fetched instruction. For instance, the decode unit 804 may decode the fetched instruction into a plurality of micro-operations.

Additionally, the core 706 may include a schedule unit 806. The schedule unit 806 may perform various operations associated with storing decoded instructions (e.g., received from the decode unit 804) until the instructions are ready for dispatch, e.g., until all source values of a decoded instruction become available. In one example, the schedule unit 806 may schedule and/or issue (or dispatch) decoded instructions to an execution unit 808 for execution. The execution unit 808 may execute the dispatched instructions after they are decoded (e.g., by the decode unit 804) and dispatched (e.g., by the schedule unit 806). In an example, the execution unit 808 may include more than one execution unit. The execution unit 808 may also perform various arithmetic operations such as addition, subtraction, multiplication, and/or division, and may include one or more an arithmetic logic units (ALUs). In an example, a co-processor (not shown) may perform various arithmetic operations in conjunction with the execution unit 808.

Further, the execution unit 808 may execute instructions out-of-order. Hence, the processor core 706 may be an out-of-order processor core in one example. The core 706 may also include a retirement unit 810. The retirement unit 810 may retire executed instructions after they are committed. In an example, retirement of the executed instructions may result in processor state being committed from the execution of the instructions, physical registers used by the instructions being de-allocated, etc.

The core 706 may also include a bus unit 714 to enable communication between components of the processor core 706 and other components (such as the components discussed with reference to FIG. 8) via one or more buses (e.g., buses 804 and/or 812). The core 706 may also include one or more registers 816 to store data accessed by various components of the core 706 (such as values related to power consumption state settings).

Furthermore, even though FIG. 7 illustrates the control unit 720 to be coupled to the core 706 via interconnect 812, in various examples the control unit 720 may be located elsewhere such as inside the core 706, coupled to the core via bus 704, etc.

Figure 9:
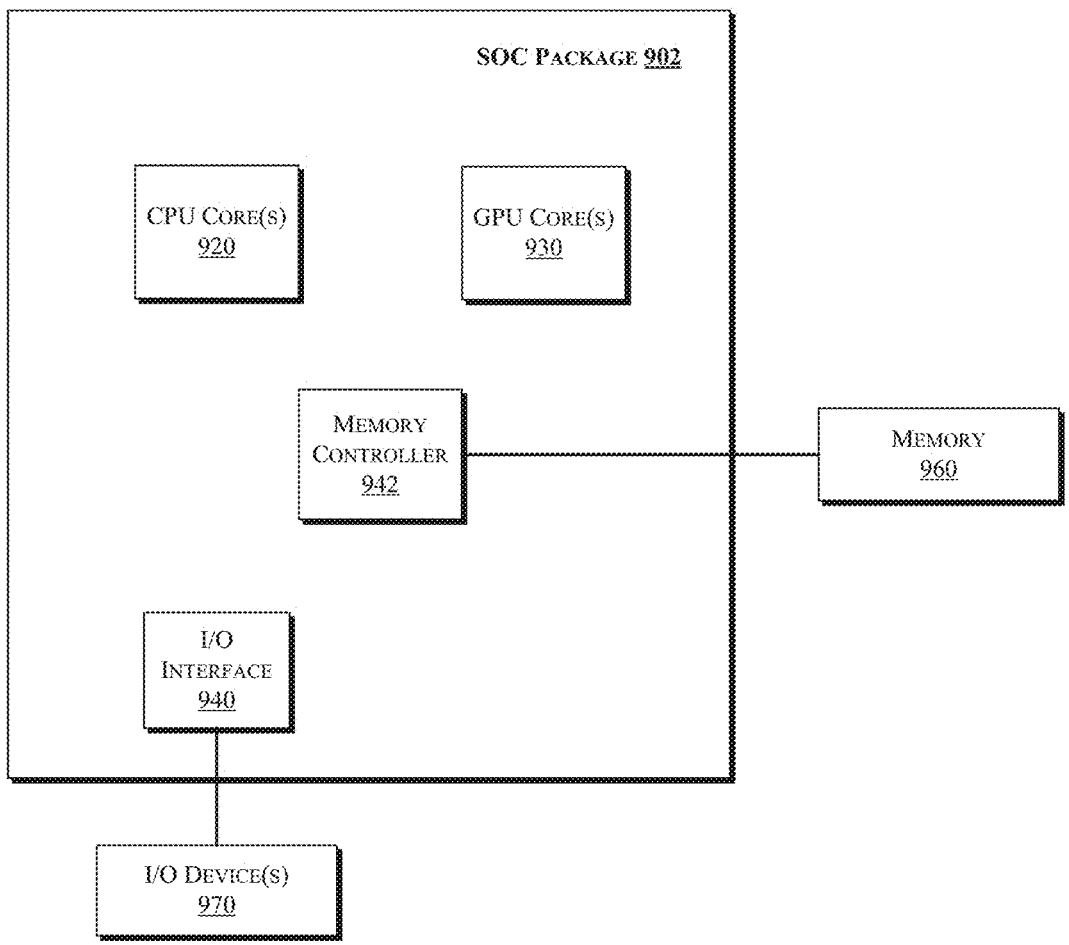

In some examples, one or more of the components discussed herein can be embodied as a System On Chip (SOC) device. FIG. 9 illustrates a block diagram of an SOC package in accordance with an example. As illustrated in FIG. 9, SOC 902 includes one or more processor cores 920, one or more graphics processor cores 930, an Input/Output (I/O) interface 940, and a memory controller 942. Various components of the SOC package 902 may be coupled to an interconnect or bus such as discussed herein with reference to the other figures. Also, the SOC package 902 may include more or less components, such as those discussed herein with reference to the other figures. Further, each component of the SOC package 902 may include one or more other components, e.g., as discussed with reference to the other figures herein. In one example, SOC package 902 (and its components) is provided on one or more Integrated Circuit (IC) die, e.g., which are packaged into a single semiconductor device.

As illustrated in FIG. 9, SOC package 902 is coupled to a memory 960 (which may be similar to or the same as memory discussed herein with reference to the other figures) via the memory controller 942. In an example, the memory 960 (or a portion of it) can be integrated on the SOC package 902.

The I/O interface 940 may be coupled to one or more I/O devices 970, e.g., via an interconnect and/or bus such as discussed herein with reference to other figures. I/O device(s) 970 may include one or more of a keyboard, a mouse, a touchpad, a display, an image/video capture device (such as a camera or camcorder/video recorder), a touch surface, a speaker, or the like.

Figure 10:
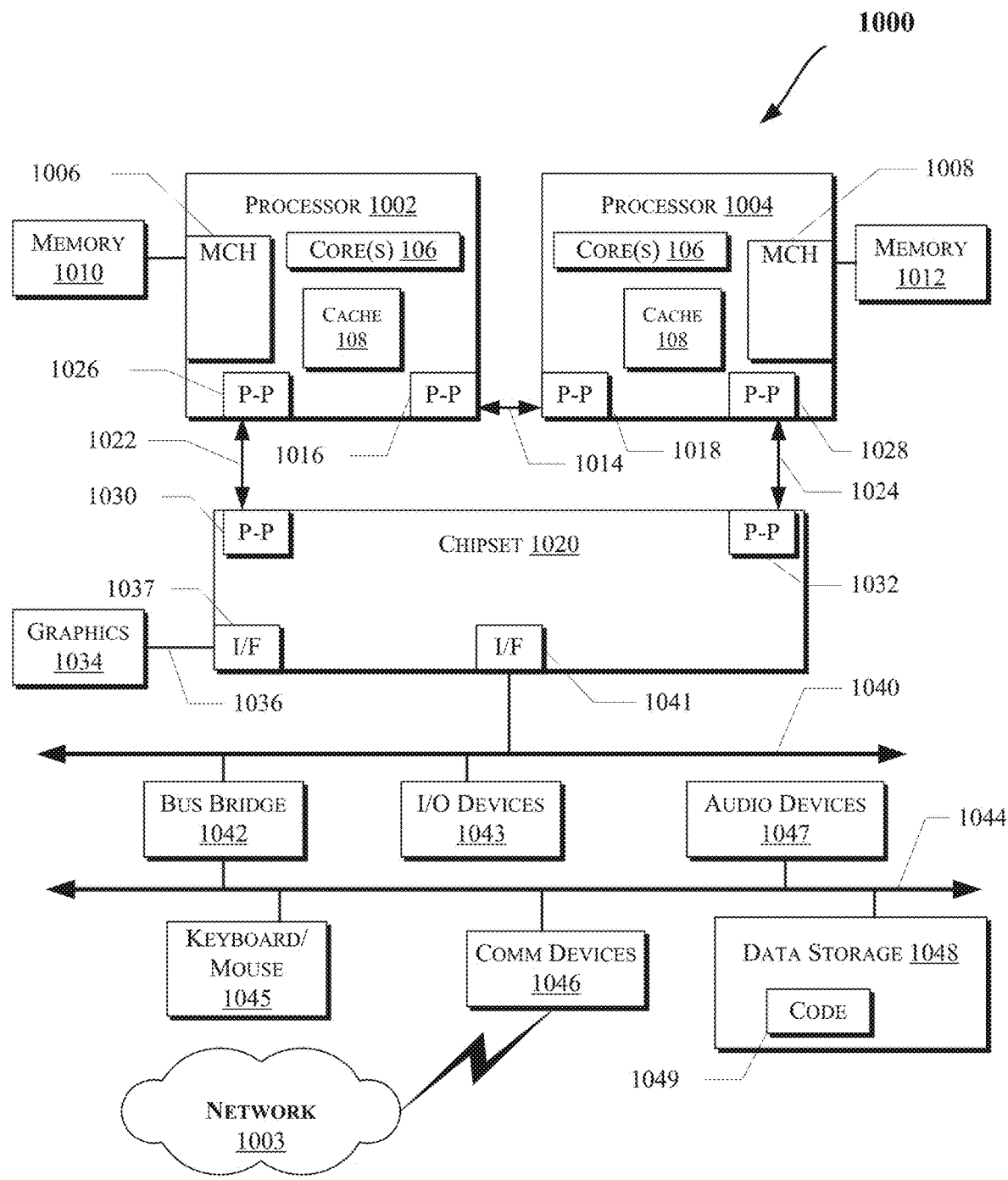

FIG. 10 illustrates an information processing system 1000 that is arranged in a point-to-point (PtP) configuration, according to an example. In particular, FIG. 10 shows a system where processors, memory, and input/output devices are interconnected by a number of point-to-point interfaces.

As illustrated in FIG. 10, the system 1000 may include several processors, of which only two, processors 1002 and 1004 are shown for clarity. The processors 1002 and 1004 may each include a local memory controller hub (MCH) 1006 and 1008 to enable communication with memories 1010 and 1012.

In an example, the processors 1002 and 1004 may be one of the processors 702 discussed with reference to FIG. 7. The processors 1002 and 1004 may exchange data via a point-to-point (PtP) interface 1014 using PtP interface circuits 1016 and 1018, respectively. Also, the processors 1002 and 1004 may each exchange data with a chipset 1020 via individual PtP interfaces 1022 and 1024 using point-to-point interface circuits 1026, 1028, 1030, and 1032. The chipset 1020 may further exchange data with a high-performance graphics circuit 1034 via a high-performance graphics interface 1036, e.g., using a PtP interface circuit 1037.

The chipset 1020 may communicate with a bus 1040 using a PtP interface circuit 1041. The bus 1040 may have one or more devices that communicate with it, such as a bus bridge 1042 and I/O devices 1043. Via a bus 1044, the bus bridge 1043 may communicate with other devices such as a keyboard/mouse 1045, communication devices 1046 (such as modems, network interface devices, or other communication devices that may communicate with the computer network 1003), audio I/O device, and/or a data storage device 1048. The data storage device 1048 (which may be a hard disk drive or a NAND flash based solid state drive) may store code 1049 that may be executed by the processors 1004.

The following pertains to further examples.

Example 1 is an input device for an electronic device, comprising a first panel comprising an array of pressure sensors, a second panel comprising an array of apertures in fluid communication with the pressure sensors, and a controller comprising logic, at least partly including hardware logic, to receive a plurality of output signals from the plurality of pressure sensors, determine, from the plurality of output signals, a location of an input on the second panel, and generate a data point on a bitmap corresponding to the location of the input on the second panel.

In Example 2, the subject matter of Example 1 can optionally include an arrangement in which the first panel comprises a two-dimensional array of pressure sensors.

In Example 3, the subject matter of any one of Examples 1-2 can optionally include a plurality of ducts extending between the array of pressure sensors and the array of apertures.

In Example 4, the subject matter of any one of Examples 1-3 can optionally include the array of pressure sensors comprises a first number of pressure sensors and the array of apertures comprises a second number of apertures, greater than the first number of pressure sensors.

In Example 5, the subject matter of any one of Examples 1-4 can optionally include logic, at least partially including hardware logic, configured to collect a time series data set of locations of input signals from the plurality of pressure sensors over a period of time; and map the time series data set of locations onto a pattern on a bitmap.

In Example 6, the subject matter of any one of Examples 1-5 can optionally include logic, at least partially including hardware logic, configured to apply a smoothing factor to time series data set.

In Example 7, the subject matter of any one of Examples 1-6 can optionally include logic, at least partially including hardware logic, configured to generate an output corresponding to a symbol when the pattern on the bitmap corresponds to the symbol.

In Example 8, the subject matter of any one of Examples 1-7 can optionally include logic, at least partially including hardware logic, configured to compare the pattern on the bitmap to a plurality of patterns stored in a memory coupled to the controller.

In Example 9, the subject matter of any one of Examples 1-8 can optionally include a display device communicatively coupled to the controller.

In Example 10, the subject matter of any one of Examples 1-9 can optionally include logic, at least partially including hardware logic, configured to generate an output on the display device corresponding to the pattern on the bitmap.

Example 11 is an input device for an electronic device, comprising a first panel comprising an array of microphones, a second panel comprising an array of boots in fluid communication with the microphones, and a controller comprising logic, at least partly including hardware logic, to receive a plurality of output signals from the plurality of pressure microphones, determine, from the plurality of output signals, a location of an input on the second panel, and generate a data point on a bitmap corresponding to the location of the input on the second panel.

In Example 12, the subject matter of Example 11 can optionally include an arrangement in which the first panel comprises a two-dimensional array of microphones.

In Example 13, the subject matter of any one of Examples 10-12 can optionally include an arrangement in which the plurality of boots are formed in a plurality of different configurations to generate a plurality of different frequency outputs in response to airflow incident upon the respective boots.

In Example 14, the subject matter of any one of Examples 10-13 can optionally include an arrangement in which the plurality of boots are formed in a plurality of different configurations to generate a plurality of different frequency outputs in response to airflow incident upon the respective boots.

In Example 15, the subject matter of any one of Examples 10-14 can optionally include an arrangement in which the array of microphones comprises a first number of microphones and the array of boots comprises a second number of boots, equal to the first number of microphones.

In Example 16, the subject matter of any one of Examples 10-15 can optionally include logic, at least partially including hardware logic, configured to collect a time series data set of locations of input signals from the plurality of microphones over a period of time; and map the time series data set of locations onto a pattern on a bitmap.

In Example 17, the subject matter of any one of Examples 10-15 can optionally include logic, at least partially including hardware logic, configured to apply a smoothing factor to time series data set.

In Example 17, the subject matter of any one of Examples 10-16 can optionally include logic, at least partially including hardware logic, configured to generate an output corresponding to a symbol when the pattern on the bitmap corresponds to the symbol.

In Example 18, the subject matter of any one of Examples 10-17 can optionally include logic, at least partially including hardware logic, configured to compare the pattern on the bitmap to a plurality of patterns stored in a memory coupled to the controller.

in Example 19, the subject matter of any one of Examples 10-18 can optionally include logic, at least partially including hardware logic, configured to a display device communicatively coupled to the controller.

In Example 20, the subject matter of any one of Examples 10-19 can optionally include logic, at least partially including hardware logic, configured to generate an output on the display device corresponding to the pattern on the bitmap.

Example 21 is a computer program product comprising logic instructions stored on a non-transitory computer readable medium which, when executed by a controller, configure the controller to receive a plurality of output signals from a plurality of sensors on a panel, determine, from the plurality of output signals, a location of an input on the panel, and generate a data point on a bitmap corresponding to the location of the input on the panel.

In Example 22, the subject matter of Example 21 can optionally include logic, at least partly including hardware logic, to apply a smoothing factor to time series data set.

In Example 23, the subject matter of any one of Examples 21-22 can optionally include logic, at least partly including hardware logic, to generate an output corresponding to a symbol when the pattern on the bitmap corresponds to the symbol.

In Example 24, the subject matter of any one of Examples 21-23 can optionally include logic, at least partially including hardware logic, configured to compare the pattern on the bitmap to a plurality of patterns stored in a memory coupled to the controller.

In Example 25, the subject matter of any one of Examples 21-24 can optionally include logic, at least partially including hardware logic, configured to generate an output on a display device corresponding to the pattern on the bitmap.

The terms "fluid communication" as referred to herein should be construed broadly to encompass an arrangement which allows a fluid, e.g., a gas or a liquid, to pass between a first object and a second object. Thus, two objects in fluid communication may be in a direct physical connection. Alternatively, two objects in fluid communication may be coupled by a passageway through which a fluid may pass.

The terms "logic instructions" as referred to herein relates to expressions which may be understood by one or more machines for performing one or more logical operations. For example, logic instructions may comprise instructions which are interpretable by a processor compiler for executing one or more operations on one or more data objects. However, this is merely an example of machine-readable instructions and examples are not limited in this respect.

The terms "computer readable medium" as referred to herein relates to media capable of maintaining expressions which are perceivable by one or more machines. For example, a computer readable medium may comprise one or more storage devices for storing computer readable instructions or data. Such storage devices may comprise storage media such as, for example, optical, magnetic or semiconductor storage media. However, this is merely an example of a computer readable medium and examples are not limited in this respect.

The term "logic" as referred to herein relates to structure for performing one or more logical operations. For example, logic may comprise circuitry which provides one or more output signals based upon one or more input signals. Such circuitry may comprise a finite state machine which receives a digital input and provides a digital output, or circuitry which provides one or more analog output signals in response to one or more analog input signals. Such circuitry may be provided in an application specific integrated circuit (ASIC) or field programmable gate array (FPGA). Also, logic may comprise machine-readable instructions stored in a memory in combination with processing circuitry to execute such machine-readable instructions. However, these are merely examples of structures which may provide logic and examples are not limited in this respect.

Some of the methods described herein may be embodied as logic instructions on a computer-readable medium. When executed on a processor, the logic instructions cause a processor to be programmed as a special-purpose machine that implements the described methods. The processor, when configured by the logic instructions to execute the methods described herein, constitutes structure for performing the described methods. Alternatively, the methods described herein may be reduced to logic on, e.g., a field programmable gate array (FPGA), an application specific integrated circuit (ASIC) or the like.

In the description and claims, the terms coupled and connected, along with their derivatives, may be used. In particular examples, connected may be used to indicate that two or more elements are in direct physical or electrical contact with each other. Coupled may mean that two or more elements are in direct physical or electrical contact. However, coupled may also mean that two or more elements may not be in direct contact with each other, but yet may still cooperate or interact with each other.

Reference in the specification to "one example" or "some examples" means that a particular feature, structure, or characteristic described in connection with the example is included in at least an implementation. The appearances of the phrase "in one example" in various places in the specification may or may not be all referring to the same example.

Although examples have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. An input device for an electronic device, comprising:
    a first panel comprising an array of pressure sensors arranged in a two-dimensional array, at least one sensor in the array of pressure sensors communicatively coupled to an operating voltage source and to a ground to generate an output signal that is a function of a pressure applied to the sensor;
    a second panel formed from a rigid material and comprising an array of ducts which provide an airflow passage to the array of pressure sensors on the first panel; and
    a controller comprising logic, at least partly including hardware logic, to:
        receive a plurality of output signals from the plurality of pressure sensors;
        apply a smoothing factor to time series data set, the smoothing factor to filter outputs from one or more pressure sensors that are of substantially greater magnitude than an average output from the array of pressure sensors;
        determine, from the plurality of output signals, a location of an input on the second panel; and
        generate a data point on a bitmap corresponding to the location of the input on the second panel.

2. The input device of claim 1, wherein the first panel comprises a two-dimensional array of pressure sensors.

3. The input device of claim 1, further comprising a plurality of ducts extending between the array of pressure sensors and the array of apertures.

4. The input device of claim 1, wherein the array of pressure sensors comprises a first number of pressure sensors and the array of apertures comprises a second number of apertures, greater than the first number of pressure sensors.

5. The input device of claim 1, wherein the controller further comprises logic, at least partially including hardware logic, to:
    collect a time series data set of locations of input signals from the plurality of pressure sensors over a period of time; and
    map the time series data set of locations onto a pattern on a bitmap.

6. The input device of claim 5, wherein the controller further comprises logic, at least partially including hardware logic, to:
    generate an output corresponding to a symbol when the pattern on the bitmap corresponds to the symbol.

7. The input device of claim 6, wherein the controller further comprises logic, at least partially including hardware logic, to:
    compare the pattern on the bitmap to a plurality of patterns stored in a memory coupled to the controller.

8. The input device of claim 5, further comprising a display device communicatively coupled to the controller.

9. The input device of claim 8, wherein the controller further comprises logic, at least partially including hardware logic, to:
    generate an output on the display device corresponding to the pattern on the bitmap.

* * * * *